United States Patent [19]
Field, Jr. et al.

[11] Patent Number: 5,241,170
[45] Date of Patent: Aug. 31, 1993

[54] FIBER OPTIC IMAGING DEVICE AND METHODS

[75] Inventors: Robert J. Field, Jr., Fincastle; Peter L. Toch, Roanoke, both of Va.

[73] Assignee: ITT Corporation, New York, N.Y.

[21] Appl. No.: 838,550

[22] Filed: Feb. 19, 1992

[51] Int. Cl.$^5$ ............................................. H01J 40/14
[52] U.S. Cl. .............................. 250/214 VT; 250/226; 250/227.2; 606/15
[58] Field of Search ......... 250/227.2, 213 VT, 213 R, 250/226; 385/117; 313/524; 128/660.07; 606/7, 14, 15

[56] References Cited

U.S. PATENT DOCUMENTS

| | | | |
|---|---|---|---|
| 3,987,299 | 10/1976 | Mulder | 250/213 VT |
| 4,374,325 | 2/1983 | Howorth | 250/213 VT |
| 4,460,826 | 7/1984 | Pryor | 250/227.2 |
| 4,556,057 | 12/1985 | Hiruma et al. | 606/14 |
| 4,631,582 | 12/1986 | Nagasaki et al. | 358/98 |
| 4,669,467 | 6/1987 | Willet et al. | 606/15 |

OTHER PUBLICATIONS

Profio, Florescence Bronchoscopy for Localization of Carcinoma in situ, Jan./Feb. 1983, Med. Phys. 10(1) pp. 35–39.

Primary Examiner—David C. Nelms
Assistant Examiner—K. Shami
Attorney, Agent, or Firm—Arthur L. Plevy; Patrick M. Hogan

[57] ABSTRACT

A fiber optic viewing device has in a first embodiment, a color-preserving image intensifier positioned at the viewing end thereof. In a second embodiment, an input light source is sequentially modulated through a cycle of wavelength sets. The resulting image is intensified and recolored by an output recoloring filter which is synchronized with the input light modulation. In yet another embodiment, a set of red, green and blue LEDs are sequentially modulated by a controller to provide input light. A CCD camera receives the resultant intensified image and converts it to video format. A video processor stores frames during a cycle of modulation and then integrates the frames for viewing in full color.

54 Claims, 4 Drawing Sheets

FIBER OPTIC IMAGING DEVICE AND METHODS

FIELD OF THE INVENTION

The present invention relates to fiber optic imaging apparatus, such as, endoscopes, proctoscopes, laparoscopes, etc. and, more particularly, to such apparatus having the capability to produce an amplified color output image.

DESCRIPTION OF THE RELATED ART

There are numerous imaging devices which utilize a fiber optic bundle. These bundles are normally thin and elongated and permit the bundle to be inserted into small openings and passageways to position the objective end near otherwise inaccessible objects for viewing. Thus, fiber optics have found wide application for examination of the human body as employed as catheters, in that they provide a relatively nonobtrusive means for examining internal anatomy, e.g., the lungs, nasal passageways, veins, etc. Further, these viewing instruments, e.g., endoscopes, proctoscopes, bronchoscopes, laparoscopes, mediastinoscopes, etc., are frequently employed for assisting in the performance of diagnostic and treatment procedures, such as, e.g., placement of endotracheal tubes and surgery and therefore are frequently accompanied by cutting, inflating, washing, etc. devices which are incorporated into a single instrument with the optical bundle. Of course, the use of fiber optic bundles is not limited to medical applications in humans, such apparatus having equivalent utility in the veterinary treatment of animals and for viewing any inaccessible structure, e.g., the interior of a mechanical device.

In most instances, fiber optic viewing devices include a source of illumination and at least one fiber optic fiber, a "light pipe", for conducting light from the illumination source to the objective end of the fiber optic bundle where it is projected upon the field of view and illuminates the object(s) under study. The light projected upon the field of view from the light pipe is reflected off the objects in the field of view and enters the objective end of the fiber optic bundle for transmission to a viewing eyepiece. In some instruments, a portion of the image, e.g., 10%, is split off for recording by video processing equipment, e.g., video recording camera. If a white light illumination source is used, light of all wavelengths of the visible spectrum is projected upon the field of view and objects of different color reflect back corresponding wavelengths. In this circumstance, the output image would be appropriately colored. Of course, color is an important factor in identifying and discerning different objects having different properties and significance. For example, cancerous growth or plaque deposits are likely to have a different color than adjacent healthy tissue.

Because most fiber optic viewers merely transmit the image from the field of view to the viewer without image processing, other than perhaps magnification with an optical lens, these devices can be described as "direct view" devices. There are certain important limitations inherent in "direct view" fiber optic apparatus, particularly as applied to the medical arts. One such limitation is the small cross sectional area of the tip of the viewing fiber optic bundle at the objective end. The tip is preferably as small as possible to permit introduction of the bundle into the smallest possible openings. This small tip cross-section also limits the quantity of light that may be collected at the tip, however, reducing image brightness. To compensate for a small light collection aperture, the illuminating light intensity supplied to the light pipe is increased. The illuminating light intensity has an upper useable limit, however, due to the unwanted side effects of heating and tissue damage which may occur from using excessively bright illuminating light sources. A further limitation in known fiber optic imaging devices is a limitation on resolution resulting from a limitation on the number of optical fibers for a given cross-sectional area. The limitation on fiber density, i.e., number of fibers in a given cross-sectional area, arises due to optical losses in fibers smaller in diameter than a minimum workable fiber size. It has been found, e.g., that fibers less than 10 um exhibit unacceptable optical losses in direct view devices. In addition to limitations in fiber diameter, there is the limitation in number of fibers, owing to the limitation in overall bundle diameter, such as that which is inherent in a fiber optic bundle for insertion into a vein, for example. The use of accompanying instruments for manipulating, inflating, cutting or injecting within a common sheath with the fiber optic bundle further limits overall bundle size. As a result of all the foregoing factors and limitations, image output intensity and resolution may both be severely limited.

Devices are known in the fields of radiology and optics wherein ambient light images are increased in brightness through a variety of image intensifier apparatus. For example, the military relies heavily on image intensifiers to allow tactical operations to be conducted at night, using "night vision goggles" and the like. The operating principles of these image intensifiers are well known.

One limiting aspect of such image intensifiers is that they are inherently color-blind. That is, the cathode material of the image intensifier produces only one electron per photon event, no matter what color the photon may be. The number of electrons and electron energies are amplified without regard to the color of the original photon. The output of the image intensifier (I2) is typically a direct view of a monochromatic (usually green) phosphor, or a monochrome television signal using a CCD camera, either coupled to the phosphor or driven by the amplified electrons (Electron-Bombarded CCD).

Applicants are aware of one instance where the combination of an image intensifier with a fiber optic viewer was proposed for enhancing the intensity of a fluorescent emission image during fluorescence bronchoscopy. That is, only emissions of a specific wavelength which were received by the fiber optic viewer were intensified. This combination was proposed by Profio, Doiron, Balchum and Huth of the University of Southern California Institute for Physics and Imaging Science and reported in Med. Phys. 10(1), January/February, 1983. This combination was not amenable to use for viewing the entire image presented at the objective of the fiber optic, i.e., all wavelengths, because of the inherent color-blindness of image intensifiers. Accordingly, provision was made for direct viewing without image intensification when normal colorization was desired.

Methods for generating color output images with an image intensifier have been described by one of the inventors herein, Robert Jett Field, Jr. in U.S. patent application Ser. No. 07/662,268, filed Feb. 28, 1991 and entitled COLOR IMAGE INTENSIFIER DEVICE and in U.S patent application Ser. No. 07/736,716, filed Jul. 26, 1991, entitled COLOR IMAGE INTENSIFIER DEVICE AND METHOD FOR PRODUCING SAME. The first of the foregoing applications relating to an image intensifier fitted with a pair of moveable color members each having a plurality of color segments or portions for passing different light frequencies therethrough. One moveable, e.g., rotatable, color member is positioned over the input of the intensifier and the other is positioned over the output. The members are moved in synchronicity, such that incident light passing through the first member is amplified and appropriately recolored upon output from the intensifier and passage through the second member.

In the other aforementioned application by Mr. Field, a device and method are described wherein a filter matrix with a plurality of sets of primary color filters is positioned on the input of an intensifier. A corresponding matrix of colorizing elements is positioned on the output of the intensifier to recolor the monochrome output of the intensifier.

To the best of applicant's knowledge, neither real image (full visible spectrum) intensification nor image colorization has been applied to the fiber optic imaging art.

It is therefore an object of the present invention to provide a fiber optic viewing device which exceeds the limitations of resolution and brightness of known devices. It is a further object to provide this improved fiber optic viewing device without loss of color imaging. It is yet another object of the present invention to provide false color imaging through a fiber optic viewing device.

SUMMARY OF THE INVENTION

The problems and disadvantages associated with conventional fiber optic viewing devices having a light pipe for conducting light to a field of view and a fiber optic bundle for transmitting an image of the field of view from an objective end to a viewing end thereof and methods for operating same are overcome by the present invention which includes a light source for radiating light into the light pipe. An image intensifier is positioned proximate the viewing end to receive and intensify the image transmitted. Means for coloring the intensified image are provided.

BRIEF DESCRIPTION OF THE FIGURES

For a better understanding of the present invention, reference is made to the following detailed description of several exemplary embodiments considered in conjunction with the accompanying drawings, in which.

DETAILED DESCRIPTION OF THE FIGURES

Figure 1:
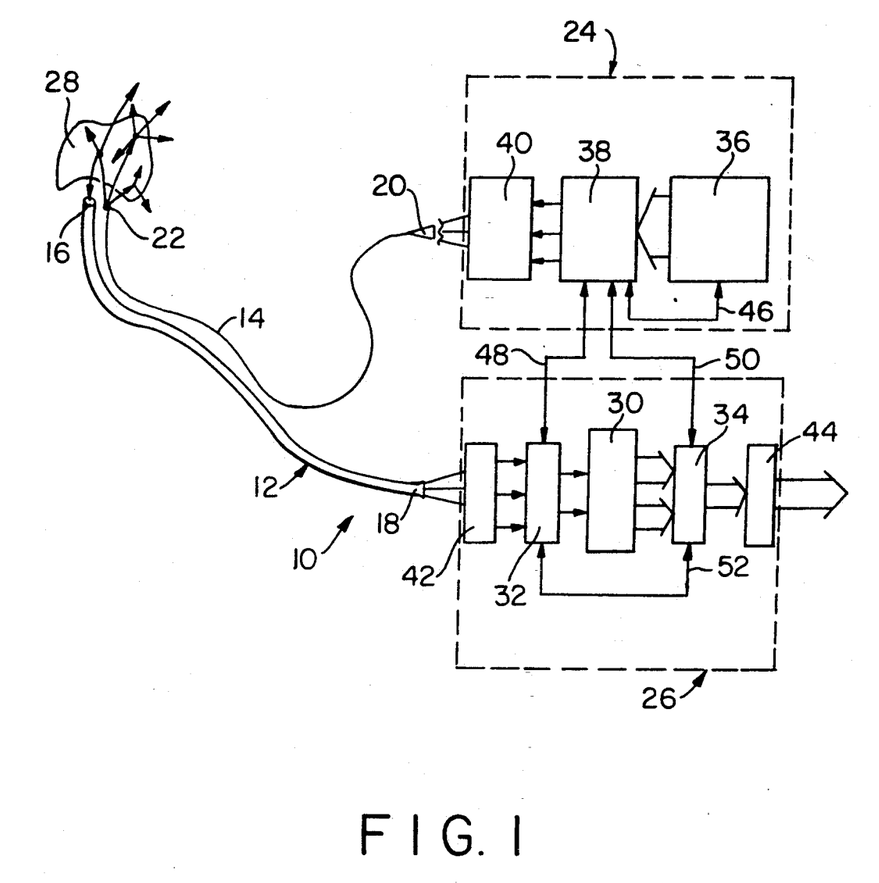
FIG. 1 is a generic diagram of an apparatus in accordance with the present invention.

FIG. 1 shows a fiber optic imaging device or viewer 10 which employs a conventional fiber optic bundle 12 and light pipe 14. The fiber optic bundle 12 has an objective end 16 for receiving images to be viewed at the viewing end 18. The light pipe 14 may include a fiber optic reducer or concentrating lens 20 for capturing and concentrating illuminating input light to be conducted down the light pipe 14 to its illuminating output end 22. As is typical for fiber optic viewing devices, the light pipe 14 and the fiber optic bundle 12 are bound together proximate their viewing end in a common sheath, cable, or within the lumen(s) of a rigid tube, which for simplicity of illustration is not shown. This binding permits the ready, simultaneous insertion of the bundle 12 and light pipe 14 and maintains the illuminating output end 22 of the light pipe 14 in position relative to the objective end 16 of the bundle 12 so that illuminating light emitted by the light pipe 14 is reflected off the object to be viewed and enters the fiber optic bundle objective end 16.

The objectives of the present invention may be achieved by either of two basic configurations, both of which include, in addition to the conventional elements described above, an illuminating light source 24 and an output image processor 26 which are depicted as dashed boxes in FIG. 1. The internal components making up the light source 24 and the output image processor 26 may be selected in a variety of combinations as shall be described more fully below. In a first basic configuration, the input light source 24 emits a constant set of wavelengths, e.g., white light. The illuminating light exits the light source 24, and enters the light pipe 14; it is then emitted from the output end 22, striking the object 28 to be viewed. Some portion of the light striking the object 28 would normally be reflected back into the objective end 16 of the fiber optic bundle and would produce an image at the viewing end 18. The image appearing at the viewing end 18 is received within the output image processor 26. In all embodiments of the present invention, the output image processor 26 includes an image intensifier 30. In each embodiment, the image intensifier 30 is color-blind and therefore provision must be made for colorization of the intensifier 30 output. The means for achieving this colorization function gives rise to the two basic types of devices contemplated by the present invention. In the first, as previously stated, the light source 24 provides a constant set of wavelengths, for instance, white light. White illumination light results in an image produced at the viewing end 18 with normal color composition. That is, green objects appear green in the output image, red objects are red, etc. In order to realize the objectives of the invention, the image must then be intensified by the intensifier 30, but the image's color composition must be preserved in some way. In the first class of apparatus, this may be accomplished by input and output filters 32 and 34, respectively, which operate relative to the intensifier 30 in the manner described in U.S. patent application Ser. No. 07/662,268, which patent application is incorporated herein by reference or as described in U.S.

patent application Ser. No. 07/736,716 which is also incorporated herein by reference. Thus, in simplest terms, this first class of apparatus is comprised of a light source 24 emitting light of a selected approximately constant intensity and set of wavelengths and directed into the illuminating light pipe 14 of a fiber optic viewing device. The resulting output image from the fiber optic bundle 12 is passed through an input filter 32, e.g., a rotating color filter wheel having filter segments passing a set of primary colors, e.g., red, green, and blue, each segment passing a single primary color. After being subjected to filtration by the input filter, the image is intensified by the image intensifier 30. The output of the image intensifier 30 is recolorized by the output filter 34 having a similar configuration as the input filter and in synchronicity or oriented in functional and positional correspondence with it.

Figure 2A:
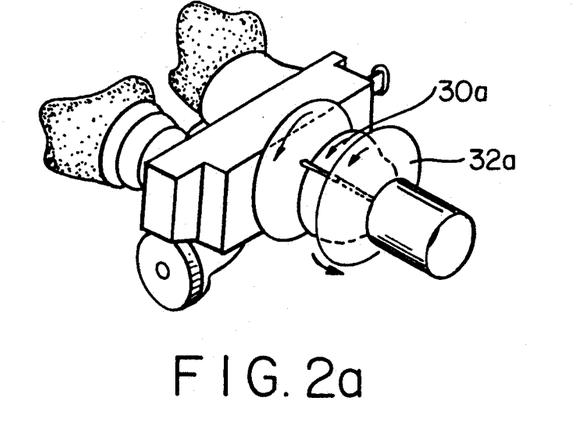
FIG. 2a is a perspective view of a color-preserving image intensifier as disclosed in U.S. patent application Ser. No. 07/662,268.
Figure 2B:
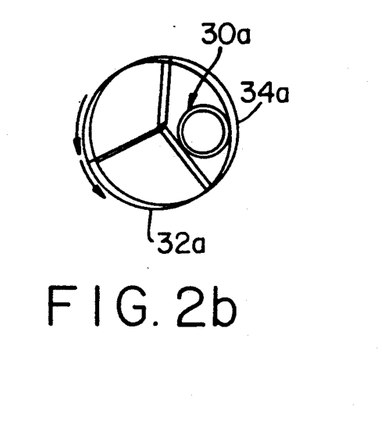
FIG. 2b is a partial elevational view of the device of FIG. 2a looking into the input aperture thereof.

FIGS. 2a-2e show color-preserving image intensifiers as disclosed in prior patent applications by one of the inventors herein, which applications are now presently pending before the patent office. FIGS. 2a and 2b illustrate rotatable color wheel input and output filters 32a and 34a, respectively, positioned at the input and output of an image intensifier 30a.

Figure 2C:
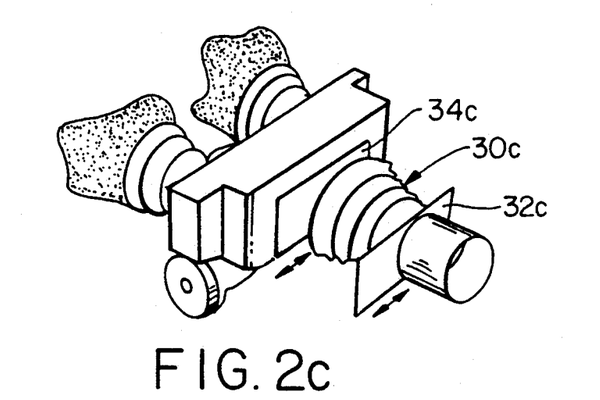
FIG. 2c is a perspective view of a color-preserving image intensifier as disclosed in U.S. patent application Ser. No. 07/662,268.
Figure 2D:
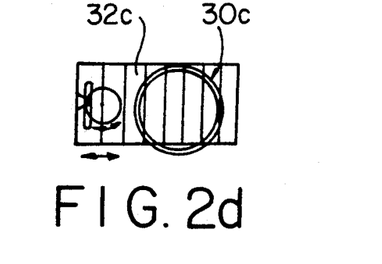
FIG. 2d is a partial elevational view of the device of FIG. 2c looking into the input aperture thereof.

FIGS. 2c and 2d illustrate segmented filter slides 32c and 34c, respectively, which oscillate rectilinearly with respect to an image intensifier 30c.

Figure 2E:
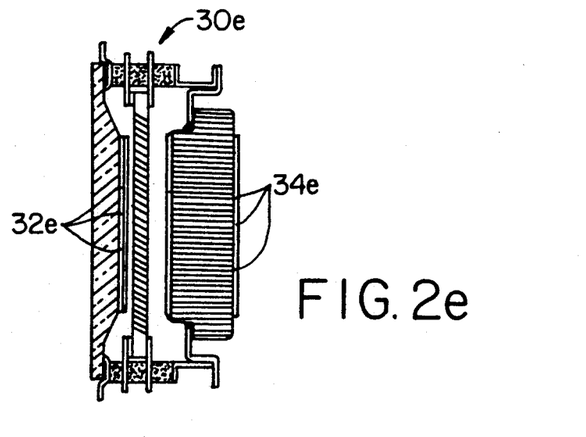
FIG. 2e is a cross-sectional view of a color-preserving image intensifier as disclosed in U.S. patent application Ser. No. 07/736,716.

FIG. 2e illustrate a color-preserving intensifier 30e having fixed input and output pixels 32e and 34e, respectively.

Apparatus of the type depicted in FIGS. 2a-2e can be utilized at the viewing end 18 of a fiber optic bundle to intensify the image while preserving color information. That is, any of the devices shown in FIGS. 2a-2e could be employed as the output image processor 26.

Referring again to FIG. 1, in this first class of apparatus, the light source would include a light generator 36 which emits light energy of a particular wavelength or set of wavelengths. The light generator could be a simple incandescent or fluorescent lamp, an ultra violet light bulb, a laser, an LED or set of LEDs, etc. After the light energy emanates from the light generator 36, an illumination light filter 38 may be employed to filter out certain wavelengths, for example, if a colored dye is injected into the body and it is desirable to view only those body parts dyed that particular color, the illumination light filter 38 could be employed to pass only that color and block all others. After exiting the filter 38 (if used), the light for illuminating purposes may be passed through an illumination light focusing element 40, for example, an optical lens, which focuses the illumination light on the light pipe input 20, which is depicted as a concentrating lens 20, causing the illumination of the field of view as previously described and the generation of an output image at the bundle viewing end 18. Upon exiting the viewing end 18, the image may be preprocessed by a lens 42 which enlarges or focuses the image upon the intensifier 30 input. Similarly, the intensifier output, after passing through colorizing filter 34, may be enlarged or focused by a final output lens 44. It should be observed that, in this first class of apparatus according to the present invention, neither the filter 38 to generator 36 interface 46, the filter 38 to filter 32 interface 48, nor the filter 38 to filter 34 interface 50 are required. The filter 32 to filter 34 interface 52 is required in that the input filter 32 and output filter 34 must be maintained either in motion or orientation relative to each other such that the function of recolorization is performed. As observed above, one exemplary expedient as set forth in the incorporated U.S. patent application Ser. No. 07/662,268, the input and output filters 32 and 34 are rotatable color wheels indexed relative to each other and turned by a common axle. In this example, the axle would be the interface 52 between filters 32 and 34.

In the second general class of apparatus contemplated by the present invention, the illuminating light produced by the light source 24 is modulated. As in the first class of apparatus, the light source 24 may produce any combination of light energy wavelengths via combinations of incandescent bulbs, fluorescent bulbs, lasers, LEDs, UV light sources, etc. The light emitted by the light source 24 is modulated in either of two ways, viz., the light generator 36 is turned on and off by filter/controller 38, in which case the filter is logical rather than physical and is implemented by an electrical control, or a continuous light beam is modulated by a modulating filter 38, such as a rotating color wheel or chopper. If the light generator is a set of LEDs or lasers, for example, the filter 38 may be either an electrical controller which turns the LEDs or lasers on and off for selected intervals or a chopper. In the case that the filter 38 is an electrical controller, interface 46 is required. The purpose for modulating the illumination light is to provide a sequence of bursts of illuminating light of different wavelengths so that the output image processor 26, which includes an output colorizer or filter 34 which is synchronized with the modulation of the illumination light can interpret and colorize an intensified output from the image intensifier 30. The synchronization of the filter 38 with the filters 32 and 34 of the output processor 26 are shown as interface lines 48 and 50. The foregoing general description of this second class of apparatus will now be illustrated by way of specific examples as shown in the embodiments illustrated in FIGS. 3, 4 and 5.

Figure 3:
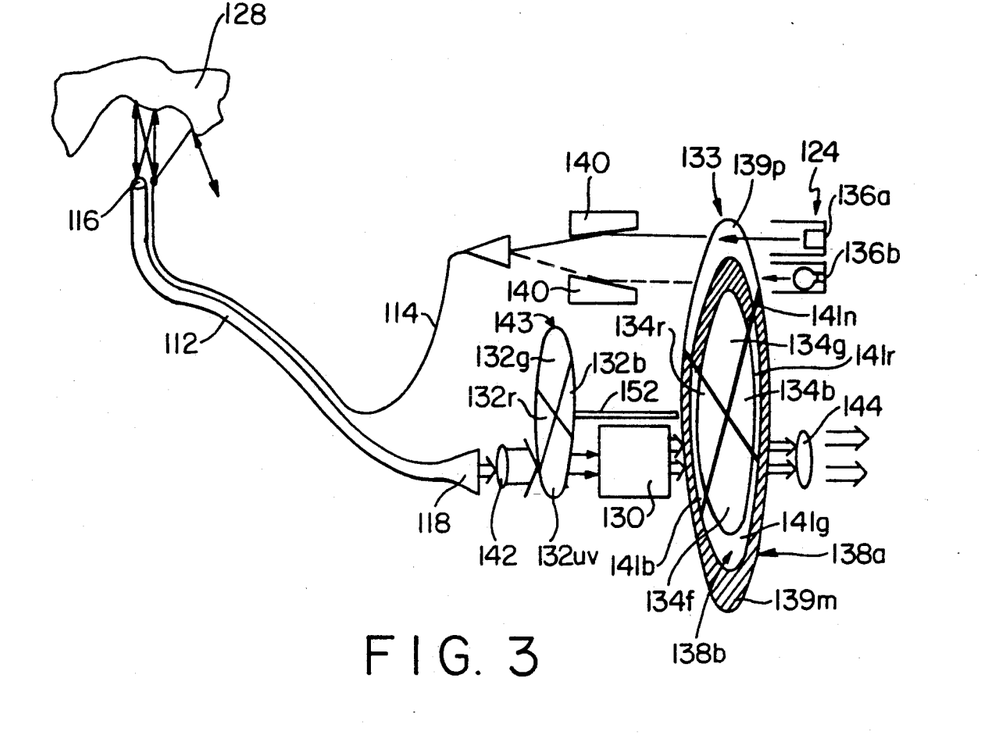
FIG. 3 is a diagram illustrating a first exemplary embodiment of the present invention.

FIG. 3 shows an apparatus in accordance with the present invention which employs modulated illumination light. The light source 124 is comprised of a U-V light bulb 136a and an incandescent (white) light bulb 136b. The bulbs 136a and 136b are positioned relative to a wheel 133 such that the light emanated from the bulbs passes through bands 138a and 138b. Filter band 138a is equivalent to a chopper, i.e., a pass/no-pass filter and is divided into a pass portion 139p and a no-pass portion 139n. Filter band 138b is also divided, but into four sections, 141r passing red light, 141g passing green light, 141b passing blue light and 141n passing no light. As can be seen, filter band 138b is both a chopper and a color filter sequentially passing discrete wavelengths of light. Besides the exterior filter bands 138a and 138b, the wheel also includes interior filter segments 134r passing red light, 134g passing green light, 134b passing blue light and 134f passing a narrow band visible wavelength producing a false color image representing u-v induced image.

If the wheel 133 is rotated, such as by an electrical motor and appropriate drive gear (not shown) the illuminating light is modulated through four phases, i.e., U-V, red, green and blue and then the phases are repeated, etc. The duration of each phase is, of course, dependent upon the speed of rotation and the relative dimensional apportionment between the alternating segments in the bands. The rate of rotation should be sufficient to eliminate excessive perceptible flicker. Having been processed by the filter bands 138a and 138b, the illumination light encounters focusing element 140, which, in this instance, is depicted as a combiner, i.e., a reflective element which redirects the alternating components of illumination light onto the input of the light pipe 114. Light entering the light pipe is conducted to and projected upon the object(s) 128 in the field of view. If the object 128 has portions which reflect or fluoresce in the illuminating light, the reflected or fluorescent light is received by the objective end 116 of the fiber optic bundle 112 and constitutes the image projected from the bundle viewing end 118. This image may then be enlarged or focused by a preprocessing lens 142. After exiting the lens 142, the image may be passed through a preintensification filter 143 which may be segmented into segments corresponding to the illumination light anticipated. In the apparatus depicted in FIG. 3, the filter 143 has three identical clear segments 132r, 132g and 132b which pass all wavelengths and a fourth segment 132uv for filtering out selected wavelengths emitted in response to the u-v illumination phase. This pre-intensification filtration can be used in fluorescence bronchoscopy, for example, when the focus of attention is fluorescence at a specific wavelength. The filter segment 132uv can be used to narrowly select this specific fluorescence signal. The image then enters the image intensifier 130 where it is intensified, but where its color composition is lost. The intensifier output is, however, appropriately recolored by the output filter inner segments 134r, g, b, and f. Segment 134f may be selected for maximum contrast with expected indigenous colors of the field of view. A final output lens 144 may be employed to enlarge or focus the colorized image. As can be appreciated from the foregoing, the modulation of the illuminating light is synchronized with the recolorization of the output image from the intensifier 130. Further, the input filtration by filter 132 is synchronized both with the modulation of illumination light and with the recolorization of the intensifier output. Thus, in terms of the diagram shown in FIG. 1, the axle would constitute the interface 52 between filter elements 32 and 34. The layout of wheel 133 with exterior bands 138a and b and interior segments 134r, g, b, and f constitutes the interface 48 and 50.

Figure 4:
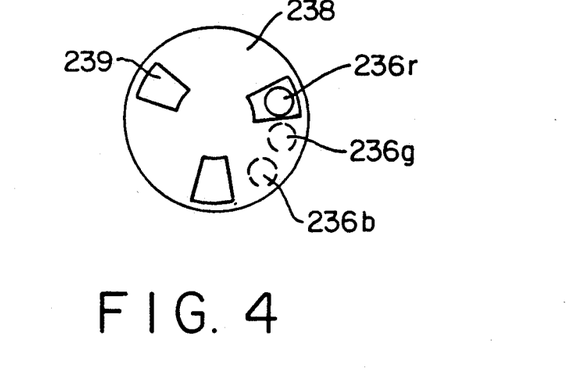
FIG. 4 is an elevational view of a laser/chopper light source employed in a second exemplary embodiment of the present invention.

FIG. 4 shows an alternative means for modulating illumination light, viz., the combination of lasers 236r, 236g and 236b and a rotating chopper wheel 238 with apertures 239. With respect to the incorporation of the lasers and chopper shown in FIG. 4 into a device like that shown in FIG. 3, it should be apparent that the chopper 238 could include interior filter segments like 134r, g, b and f and could then easily replace filter wheel 133. Alternatively, the chopper 238 could be driven in sychronicity with an independent output filter like that shown as element 34 in FIG. 1.

Figure 5:
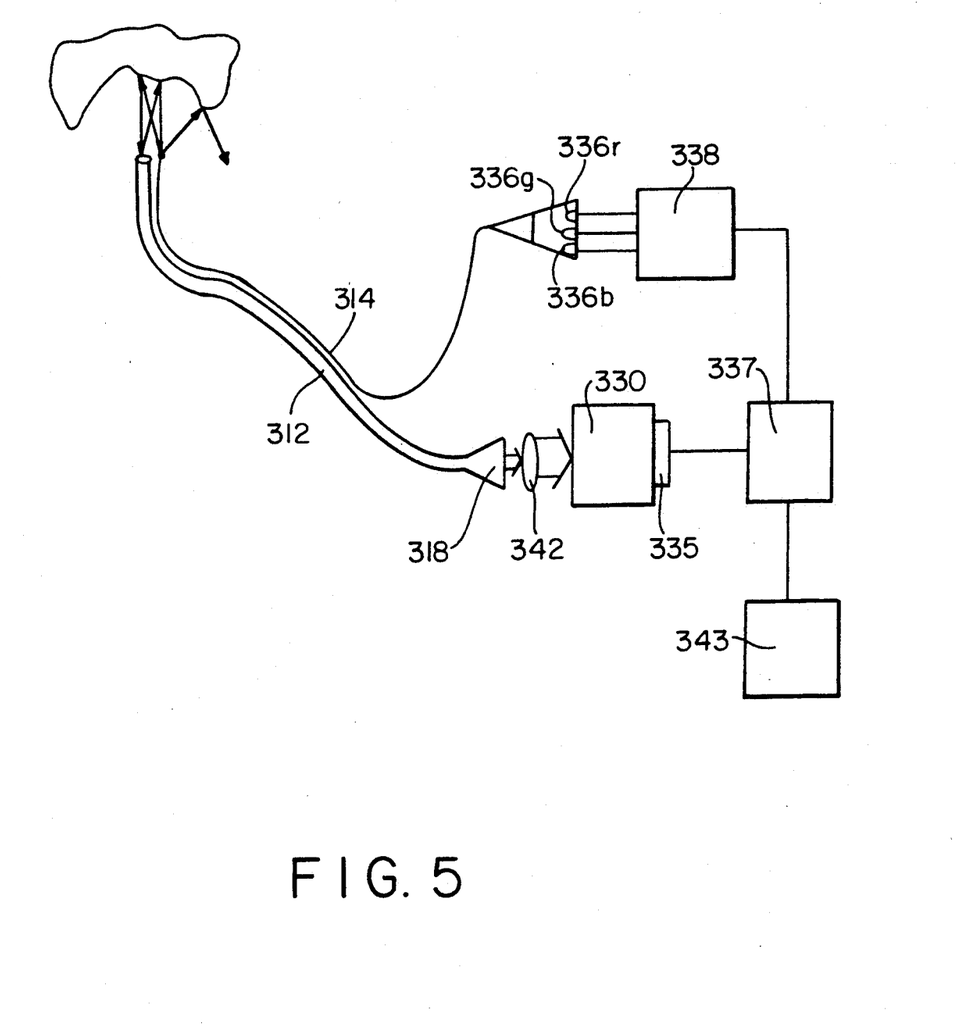
FIG. 5 is a diagram of a third exemplary embodiment of the present invention.

FIG. 5 shows yet another embodiment of the present invention wherein a set of LEDs 336r emitting red light, 336g emitting green light and 336b emitting blue light constitute the illumination light generators. The LEDs are controlled by controller 338, which switches each LED on in a predetermined sequence for a selected duration. Light from the LEDs enters the light pipe 314 and generates an image at the output 318 of the fiber optic bundle 312. The output image may be enlarged or focused upon an image intensifier 330 input by lens 342. The intensifier 330 intensifies the image and the output is received by a CCD 335 which converts the image to a video signal. The video signal is transmitted to video processing electronics. One LED is switched on at a time. While an LED is on, the CCD camera integrates one frame which is transferred to and stored by the video electronics. When three frames have been stored (corresponding to red, green and blue) they are processed into a single frame of color video output which is then displayed on a video monitor 343. As is known in the art, color sets other than red, green and blue may be employed to produce a full color image, e.g., red, yellow and green.

The color wheel and chopper methods may also be used with a CCD camera by synchronizing the frame rate with the wheel rotation.

A great advantage which is realized in this second general class of apparatus wherein illuminating light is modulated is that the field of view is subjected to less light radiation at any moment in time. That is, if only blue wavelength radiation is sent down the light pipe, the field of view is not subjected to the power of red and green light which would normally be present is white light were used to illuminate the field of view.

It should be appreciated that the embodiments described herein are merely exemplary and that a person skilled in the art may make many variations and modifications without departing from the spirit and scope of the invention as defined in the appended claims.

We claim:

1. A fiber optic imaging device having a light pipe for conducting light to a field of view and a fiber optic bundle for transmitting an image of the field of view from an objective end to a viewing end thereof, comprising:
    (a) a light source for radiating light into said light pipe, said light source supplying a substantially constant set of wavelengths of light;
    (b) an image intensifier positioned proximate said viewing end to receive and intensify said image transmitted; and
    (c) means for coloring said intensified image, said coloring means including filtering means positioned between said viewing end and said image intensifier for filtering said image transmitted and output coloring means for coloring said intensified image, said filtering means having at least two portions, a first passing light in a first range of wavelengths and a second passing light in a second range of wavelengths and said output coloring means has at least two portions, a first coloring said intensified image with a first color and a second coloring said intensified image with a second color said first and second portions of said filtering means and said output coloring means being subdivided into a plurality of discrete interspersed pixels to form corresponding filtering and output coloring matrices said filtering means and said output coloring means having a fixed orientation relative to said intensifier and to each other, such that light passing through said first and second portions of said filtering means is colored by said first and second portions, respectively, of said output coloring means.

2. The device of claim 1, wherein said pixels of said output coloring means include a color filter.

3. The device of claim 1, wherein said pixels of said output coloring means include a phosphor.

4. A fiber optic imaging device having a light pipe for conducting light to a field of view and a fiber optic bundle for transmitting an image of the field of view from an objective end to a viewing end thereof, comprising:

(a) a light source for radiating light into said light pipe, said light source supplying a substantially constant set of wavelengths of light;

(b) an image intensifier positioned proximate said viewing end to receive and intensify said image transmitted; and (c) means for coloring said intensified image, said coloring means including filtering means positioned between said viewing end and said image intensifier for filtering said image transmitted and output coloring means for coloring said intensified image, said filtering means having at least two portions, a first passing light in a first range of wavelengths and a second passing light in a second range of wavelengths and said output coloring means having at least two portions, a first coloring said intensified image a first color and a second coloring said intensified image a second color said filtering means and said output coloring means movable relative to said intensifier in synchronicity with each other such that light passing through said first and second portions of said filtering means is colored by said first and second portions, respectively, of said output coloring means.

5. The device of claim 4, wherein said filtering means and said output coloring means are each color filter wheels rotated by rotating means.

6. The device of claim 4, wherein said filtering means and said output coloring means are segmented slides which are reciprocated by reciprocating means.

7. A fiber optic imaging device having a light pipe for conducting light to a field of view and a fiber optic bundle for transmitting an image of the field of view from an objective end to a viewing end thereof, comprising:

(a) a light source for radiating light into said light pipe, said light source applying a substantially constant set of wavelengths of light:

(b) an image intensifier positioned proximate said viewing end to receive and intensify said image transmitted; and (c) means for coloring said intensified image, said coloring means including filtering means positioned between said viewing end and said image intensifier for filtering said image transmitted and output coloring means for coloring said intensified image, said filtering means having three portions corresponding to three primary colors, a first passing light in a first range of wavelengths, a second passing light in a second range of wavelengths and a third passing light in a third range of wavelengths and said output coloring means has four portions, a first coloring said intensified image a first primary color, a second coloring said intensified image a second primary color, a third coloring said intensified image a third primary color and a fourth coloring said intensified image with a false color corresponding to a particular wavelength of light conducted to the field of view such that light passing through said first, second and third portions of said filtering means and said particular wavelength of light conducted to the field of view is colored by said first, second and third and fourth portions respectively, of said output coloring means.

8. A fiber optic imaging device having a light pipe for conducting light to a field of view and a fiber optic bundle for transmitting an image of the field of view from an objective end to a viewing end thereof, comprising:

(a) a light source for radiating light into said light pipe;

(b) an image intensifier positioned proximate said viewing end to receive and intensify said image transmitted; and (c) means for coloring said intensified image including means for modulating light from said light source to sequentially provide light of at least two different wavelengths for predetermined time periods and output coloring means for coloring said intensified image at least two selected output colors.

9. The device of claim 8, wherein said means for modulating and said output coloring means are synchronized such that the intensified image resulting from light of a particular wavelength of said at least two wavelengths passing through said light pipe is colorized by said output coloring means a corresponding one of said at least two selected output colors.

10. The device of claim 9, wherein said modulating means is positioned between said light source and said light pipe input and acts upon light radiated from said light source.

11. The device of claim 10, wherein said modulating means includes a moveable light filter having at least two segments with differing light transmission properties and wherein said light source radiates a substantially constant set of wavelengths.

12. The device of claim 11, wherein said output coloring means includes a moveable light filter having at least two segments and passing light of said at least two selected output colors.

13. The device of claim 12, wherein said light filter includes color filter segments passing light corresponding to said at least two wavelengths of light.

14. The device of claim 13 wherein said light source radiates white light.

15. The device of claim 14, wherein said modulating means includes a rotatable color filter wheel.

16. The device of claim 15, wherein said modulating means and said filter means are both carried on said rotatable filter wheel.

17. The device of claim 16, wherein said common wheel has a peripheral band of filter segments and an internal band of output coloring segments.

18. The device of claim 17, wherein at least one of said filter segments passes no light.

19. The device of claim 18, wherein said light source includes two discrete light sources and said peripheral filter band is divided into more than one band, each of said more than one band modulating a corresponding discrete light source.

20. The device of clam 19, wherein a first of said two discrete light sources is a source of white light and a second is a source of U-V radiation.

21. The device of claim 20, wherein said output coloring segments are four in number and include segments generating three primary colors and a segment generating a narrow wavelength corresponding to a false color representing the visual signal resulting from said U-V radiation.

22. The device of claim 12, wherein at least one of said segments passes no light.

23. The device of claim 22, wherein said light source is a laser.

24. The device of claim 23, wherein said light source includes three lasers, each emitting a different primary color.

25. The device of claim 22, wherein said light source includes a light emitting diode.

26. The device of claim 25, wherein said light source includes three light emitting diodes, each emitting a different primary color.

27. The device of claim 9, wherein said modulating means includes a controller for said light source acting directly upon said light source to modulate said illumination light by turning said light source on and off.

28. The device of claim 27, wherein said light source includes at least 2 discrete light sources which are sequentially turned on and off by said controller, each discrete light source emitting a selected set of wavelengths of light.

29. The device of claim 28, wherein said output coloring means includes a CCD positioned proximate said intensifier output to receive said intensified image for conversion into a video signal.

30. The device of claim 29, further including a video processing unit for storing successive video frames from said video signal generated by said CCD, said processing unit receiving and storing a control signal from said controller indicative of the wavelength set illuminating said field of view in association with each of said successive frames, said processing unit after a complete cycle of modulation integrating successive frames colored said at least two output colors based upon said stored control signal into a single colored output signal for display upon a video monitor.

31. The device of claim 30, wherein said at least two output colors are three primary colors.

32. The device of claim 27, wherein said discrete light sources include at least two lasers.

33. The device of claim 27, wherein said discrete light sources include at least two LEDs.

34. A method for viewing objects with a fiber optic imaging device having a light pipe for conducting light to a field of view and a fiber optic bundle for transmitting an image of the field of view from an objective end to a viewing end thereof, comprises the steps of:
(a) radiating light into said light pipe;
(b) intensifying an image received from said viewing end of said fiber optic bundle with an image intensifier; and
(c) colorizing an intensified output image form said intensifier by filtering said image from said viewing end through at least two input filters, each passing a different range of wavelengths, before said image enters said intensifier and coloring said output image at least two different output colors, each output color corresponding to an associated one of said at least two ranges of wavelengths.

35. The method of claim 34, wherein said at least two input filters are rigidly held proximate an input of said intensifier and are each subdivided into a plurality of interspersed pixels to comprise a matrix and said step of coloring is performed by a coloring matrix having a stable juxtaposition relative to said input filter pixels and to an output of said intensifier.

36. The method of claim 35, wherein said step of coloring includes filtration of said output image through said coloring matrix, said coloring matrix having light filters.

37. The method of claim 35, wherein said step of coloring includes inducing said coloring matrix to fluoresce to form said output image.

38. The method of claim 34, wherein said at least two input filters reside on a first moveable member and said step of coloring is performed by at least two output filters residing on a second moveable member and including the step of moving said first member to sequentially filter said image from said viewing end through said at least two input filters and moving said second member in synchronicity relative to said first member.

39. The method of claim 38, wherein said first and second members are each color filter wheels and said step of moving includes rotating said first and second members.

40. The method of claim 38, wherein said first and second members are each segmented color filter slides and said step of moving includes moving said slides in an oscillating rectilinear motion.

41. A method for viewing objects with a fiber optic imaging device having a light pipe for conducting light to a field of view and a fiber optic bundle for transmitting an image of the field of view from an objective end to a viewing end thereof, comprises the steps of:
(a) radiating light into said light pipe, said light being modulated through at least two different ranges of wavelengths;
(b) intensifying an image received from said viewing end of said fiber optic bundle with an image intensifier; and
(c) colorizing an intensified output image from said intensifier by coloring said intensified output image with at least two selected output colors in synchronization with said step of modulating.

42. The method of claim 41, wherein said radiated light is modulated by a moveable input member having at least two portions with different light transmission characteristics.

43. The method of claim 42, wherein said input member includes at least one portion which passes no radiated light and intermittently chops said radiated light.

44. The method of claim 43, wherein said step of radiating includes radiating from at least two discrete sources of light, said step of chopping sequentially interrupting each of said discrete sources of light to produce said modulation.

45. The method of claim 44, where said at least two discrete sources include lasers.

46. The method of claim 44, wherein said at least two discrete sources include LEDs.

47. The method of claim 44, wherein said step of coloring includes filtering said intensified output image through a moveable output member having at least two output filter portions with different light transmission characteristics and further including the step of moving said output member in synchronicity with said input member.

48. The method of claim 42, wherein said at least two portions of said input member include at least two color filter segments and said step of modulation includes sequentially filtering said radiated light through said input member color filter segments.

49. The method of claim 48, wherein said step of coloring includes filtering said intensified output image through a moveable output member having at least two output filter portions passing light of at least two selected wavelengths and further including the step of moving said output member in synchronicity with said input member.

50. The method of claim 49, wherein said step of moving said output member and said input member in synchronicity is accomplished by a common color filter wheel having portions which serve as said input member and other portions of which act as said output member.

51. The method of claim 41, wherein said step of modulating includes controlling the radiation of said light source by turning said light source on and off with a controller.

52. The method of claim 51, wherein said step of controlling includes controlling at least two discrete light sources each of which radiates a different range of wavelengths by sequentially turning said discrete sources on and off.

53. The method of claim 52, wherein said step of coloring includes receiving said intensified output image with a CCD positioned proximate an output of said intensifier and converting said intensified output image into a video signal.

54. The method of claim 53, wherein said step of coloring includes storing successive video frames from said video signal in a video processing unit, said processing unit receiving and storing a control signal from said controller indicative of the wavelength set radiated by each of said discrete light sources in association with each of said successive frames, and coloring and integrating successive frames forming a complete cycle of modulation to produce a single full-colored output signal and displaying said single signal on a video monitor.

* * * * *